(12) United States Patent
Radisson et al.

(10) Patent No.: US 7,396,367 B2
(45) Date of Patent: Jul. 8, 2008

(54) DOUBLE SECONDARY PARA-PHENYLENEDIAMINE COMPOUNDS, DYE COMPOSITIONS COMPRISING SAME, AND DYEING PROCESS USING THE COMPOSITIONS

(75) Inventors: Xavier Radisson, Paris (FR); Henri Samain, Bievres (FR); Eric Metais, St. Leu la Foret (FR); Stéphane Sabelle, Paris (FR)

(73) Assignee: L'Oréal, S.A., Paris (FR)

( * ) Notice: Subject to any disclaimer, the term of this patent is extended or adjusted under 35 U.S.C. 154(b) by 289 days.

(21) Appl. No.: 11/222,238

(22) Filed: Sep. 9, 2005

(65) Prior Publication Data

US 2006/0053569 A1  Mar. 16, 2006

Related U.S. Application Data

(63) Continuation of application No. 11/022,842, filed on Dec. 28, 2004, now abandoned.

(60) Provisional application No. 60/534,369, filed on Jan. 6, 2004.

(30) Foreign Application Priority Data

Dec. 29, 2003 (FR) .................................. 03 51219

(51) Int. Cl.
  *A61Q 5/10* (2006.01)
(52) U.S. Cl. ........................ 8/405; 8/406; 8/408; 8/410; 8/411; 8/412; 8/435
(58) Field of Classification Search .................... 8/405, 8/406, 408, 410, 411, 412, 421, 435
See application file for complete search history.

(56) References Cited

U.S. PATENT DOCUMENTS

| | | | |
|---|---|---|---|
| 3,694,138 | A | 9/1972 | Kalopissis et al. |
| 4,010,200 | A | 3/1977 | Kalopissis et al. |
| 4,823,985 | A | 4/1989 | Grollier et al. |
| 5,061,289 | A | 10/1991 | Clausen et al. |
| 5,137,538 | A | 8/1992 | Madrange et al. |
| 5,380,340 | A | 1/1995 | Neunhoeffer et al. |
| 5,534,267 | A | 7/1996 | Neunhoeffer et al. |
| 5,708,151 | A | 1/1998 | Mockli |
| 5,766,576 | A | 6/1998 | Lowe et al. |
| 5,888,252 | A | 3/1999 | Mockli |
| 6,090,160 | A * | 7/2000 | Junino et al. .................... 8/409 |
| 6,099,592 | A | 8/2000 | Vidal et al. |
| 6,099,593 | A | 8/2000 | Terranova et al. |
| 6,203,579 | B1 | 3/2001 | Moeller et al. |
| 6,284,003 | B1 | 9/2001 | Rose et al. |
| 6,730,789 | B1 | 5/2004 | Birault et al. |
| 2004/0199018 | A1 | 10/2004 | Knuebel et al. |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| DE | 101 44 226 | 3/2003 |
| EP | 0 714 954 | 6/1996 |
| EP | 0 770 375 | 5/1997 |
| EP | 1 133 975 | 9/2001 |
| FR | 2 801 308 | 4/1966 |
| FR | 2 016 123 | 5/1970 |
| FR | 2 586 913 | 3/1987 |
| FR | 2 635 976 | 3/1990 |
| FR | 2 733 749 | 11/1996 |
| FR | 2 750 048 | 12/1997 |
| GB | 1026978 | 4/1966 |
| GB | 1153196 | 5/1969 |
| JP | 02-019576 | 1/1990 |
| JP | 02-174712 | 7/1990 |
| JP | 5-163124 | 6/1993 |
| JP | 2001-521559 | 11/2001 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 03/029359 | 4/2003 |

OTHER PUBLICATIONS

STIC Search Report dated Sep. 20, 2007.*
Kirk-Othmer, *Encyclopedia of Chemical Technology*, John Wiley & Songs, vol. 8, (4th ed.), pp. 542-601 (1993).
English language Derwent Abstract for DE 2 359 399. (1975).
English language Abstract for EP 0 770 375. (1975).
English language Abstract from Patent Abstracts of Japan for JP 02-019576. (1990).

(Continued)

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to double secondary para-phenylenediamine dye compounds. The present disclosure further relates to a dye composition comprising at least one double secondary para-phenylenediamine compound, a process for dyeing keratin fibers using the composition, and a kit for dyeing keratin fibers comprising a separate composition comprising an oxidizing agent.

27 Claims, No Drawings

OTHER PUBLICATIONS

English language Abstract from Patent Abstracts of Japan for JP 5-163124. (1993).
English language Abstract attached to the face of WO 94/08969 publication. (1994).

French Search Report for French Application No. 0351219 (French priority application for the present application) dated Sep. 22, 2004.

* cited by examiner

DOUBLE SECONDARY PARA-PHENYLENEDIAMINE COMPOUNDS, DYE COMPOSITIONS COMPRISING SAME, AND DYEING PROCESS USING THE COMPOSITIONS

CROSS-REFERENCE TO RELATED APPLICATION

This is a continuation of application Ser. No. 11/022,842, filed Dec. 28, 2004 which is abandoned on Nov. 8, 2005 and claims the benefit of U.S. Provisional Application No. 60/534,369, filed Jan. 6, 2004, and also claims the benefit of French Patent Application No. 03 51219, filed Dec. 29, 2003, all of which are incorporated herein by reference.

This application claims benefit of U.S. Provisional Application No. 60/534,369, filed Jan. 6, 2004.

FIELD OF THE INVENTION

The present disclosure relates to a dye composition comprising at least one double secondary para-phenylenediamine compound, and also to a process for dyeing keratin fibers using the composition. The present disclosure also relates to double secondary para-phenylenediamine compounds.

BACKGROUND OF THE INVENTION

It is known practice to dye keratin fibers, such as human hair, with dye compositions containing oxidation dye precursors, which are generally known as oxidation bases. These oxidation bases can be colorless or weakly colored compounds, which, when combined with oxidizing products, may give rise to colored compounds by a process of oxidative condensation. It is also known that the shades obtained with these oxidation bases may be varied by combining them with couplers or coloration modifiers.

The variety of molecules that may used as oxidation bases and couplers allows a wide range of colors to be obtained.

The oxidation dyeing process can comprise applying to the keratin fibers at least one base or a mixture of bases and couplers with aqueous hydrogen peroxide solution as oxidizing agent, leaving the mixture to act, and then rinsing the fibers. This process, which is generally performed at basic pH, makes it possible simultaneously to obtain dyeing and lightening of the fiber that is reflected in practice by the possibility of obtaining a final coloration that is lighter than the original color.

This type of coloration should, moreover, satisfy a certain number of requirements. Thus, it should not have toxicological drawbacks, it may be able to produce shades in the desired intensity, and may show good resistance to external agents such as light, bad weather, washing, permanent-waving, perspiration and rubbing. The dyes may also be able to cover white hairs and they may be as unselective as possible, i.e., they may produce the smallest possible differences in coloration along the same keratin fiber, which may in fact be differently sensitized (damaged) between its end and its root. They may also show good chemical stability in formulations and have a good toxicological profile.

In the field of hair dyeing, para-phenylenediamine and para-tolylenediamine are oxidation bases that are widely used. They can make it possible with oxidation couplers to obtain varied shades.

However, there is a need in the art for new oxidation bases that have a better toxicological profile than para-phenylenediamine and para-tolylenediamine, while at the same time giving the hair at least one excellent property in terms of color intensity, variety of shades, color uniformity and resistance to external agents.

DETAILED DESCRIPTION OF THE INVENTION

Accordingly, one aspect of the present disclosure are the compounds and addition salts of formula (I):

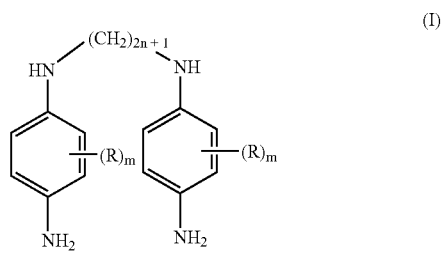

wherein:
R, which may be identical or different, is chosen from $C_1$-$C_2$ alkyl radicals; $C_1$-$C_2$ alkoxy radicals; and halogen atoms, such as chlorine;
m, which may be identical or different, is an integer ranging from 0 to 4;
n is an integer ranging from 1 to 3;
on condition that when n is equal to 1, m does not equal 0.

Another aspect of the present disclosure are dye compositions comprising, in a medium that is suitable for dyeing keratin fibers, such as human keratin fibers, at least one compound and the addition salts of formula (I'):

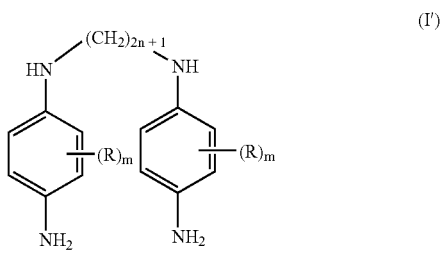

wherein:
R, which may be identical or different, is chosen from $C_1$-$C_2$ alkyl radicals; $C_1$-$C_2$ alkoxy radicals; and halogen atoms;
m, which may be identical or different, is an integer ranging from 0 to 4;
n is an integer ranging from 1 to 3.

Still another aspect of the present disclosure is a process for dyeing keratin fibers, for instance, human keratin fibers, using the compositions as disclosed herein.

The present disclosure also relates to a multi-compartment device for dyeing keratin fibers.

The dye composition as disclosed herein can make it possible to obtain strong, unselective colors that show resistance with respect to external agents.

Other characteristics and benefits of the present disclosure will emerge more clearly upon reading the description and the examples that follow.

The compound of formula (I) will first be described.

In one embodiment of the present disclosure, the compound of formula (I) is such that m is equal to 0. According to another embodiment of the present disclosure, in the compound of formula (I), n is equal to 2.

In general, the addition salts of the compound of formula (I) may be chosen, for example, from acid addition salts, such as the hydrochlorides, hydrobromides, sulfates, citrates, succinates, tartrates, lactates, tosylates, benzenesulfonates, phosphates and acetates.

The compounds of formula (I) may also be in the form of solvates, for example a hydrate or a solvate of a linear or branched $C_1$-$C_4$ alcohol such as ethanol or isopropanol.

The compounds of formula (I) may be synthesized conventionally. Reference may be made, for example, to Patent Application No. DE 101 44 226 A.

By way of non-limiting illustration, the compound may be synthesized according to the following reaction scheme:

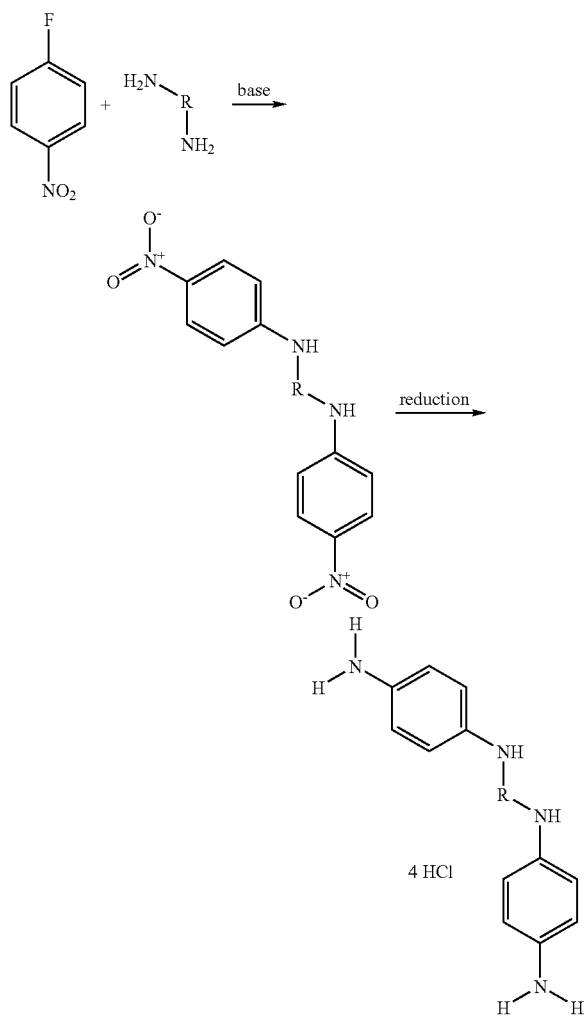

As indicated previously, another aspect of the present disclosure is a dye composition comprising, in a medium that is suitable for dyeing keratin fibers, such as human keratin fibers, at least one compound of formula (I'). According to one embodiment of the composition of the present disclosure, when n is 1 in formula (I'), m does not equal 0.

For example, in another embodiment of the composition as disclosed herein, the compound is present as oxidation base.

In accordance with yet another aspect of the present disclosure, the compound of formula (I) may be present in a dye composition in an amount ranging from 0.001% to 10% by weight, relative to the weight of the dye composition, such as from 0.005% to 6% by weight, relative to the total weight of the dye composition.

The dye composition as disclosed herein may also comprise at least one additional oxidation base other than the compound of formula (I'), optionally combined with at least one coupler and chosen from those conventionally used for dyeing keratin fibers.

By way of non-limiting example, these additional oxidation bases may be chosen from para-phenylenediamines, bis(phenyl)alkylenediamines other than those of the compound of formula (I'), para-aminophenols, bis-para-aminophenols, ortho-aminophenols, heterocyclic bases, and the addition salts thereof.

Among the para-phenylenediamines that may be used, non-limiting mention may be made of, for example, para-phenylenediamine, para-tolylenediamine, 2-chloro-paraphenylenediamine, 2,3-dimethyl-paraphenylenediamine, 2,6-dimethyl-paraphenylenediamine, 2,6-diethyl-paraphenylenediamine, 2,5-dimethyl-paraphenylenediamine, N,N-dimethyl-paraphenylenediamine, N,N-diethyl-paraphenylenediamine, N,N-dipropyl-paraphenylenediamine, 4-amino-N,N-diethyl-3-methylaniline, N,N-bis(β-hydroxyethyl)-paraphenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-paraphenylenediamine, 2-isopropyl-paraphenylenediamine, N-(β-hydroxypropyl)-paraphenylenediamine, 2-hydroxymethyl-paraphenylenediamine, N,N-dimethyl-3-methyl-paraphenylenediamine, N-ethyl-N-(β-hydroxyethyl)-para-phenylenediamine, N-(β,γ-dihydroxypropyl)-paraphenylenediamine, N-(4'-aminophenyl)-paraphenylenediamine, N-phenyl-paraphenylenediamine, 2-β-hydroxyethyloxy-para-phenylenediamine, 2-β-acetylaminoethyloxy-paraphenylenediamine, N-(β-methoxyethyl)-paraphenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the acid addition salts thereof.

Among the para-phenylenediamines mentioned above, further non-limiting mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Among the bis(phenyl)alkylenediamines that may be used, non-limiting mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,Nβ-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

Among the para-aminophenols that may be used, non-limiting mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-β-hydroxyethylaminomethyl)phenol, 4-amino-2-fluorophenol, and the acid addition salts thereof.

Among the ortho-aminophenols that may be used, non-limiting mention may be made of, for example, 2-aminophenol, 2-amino-5-methylphenol, 2-amino-6-methylphenol, 5-acetamido-2-aminophenol, and the acid addition salts thereof.

Among the heterocyclic bases that may be used, non-limiting mention may be made of, for example, pyridine derivatives, pyrimidine derivatives and pyrazole derivatives.

Among the pyridine derivatives that may be used, non-limiting mention may be made of the compounds described, for example, in British Patent Nos. GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the acid addition salts thereof.

Other pyridine oxidation bases that can be used in the compositions according to the present disclosure include the 3-aminopyrazolo[1,5-a]pyridine oxidation bases or the addition salts thereof described, for example, in French Patent Application FR 2,801,308. By way of non-limiting example, mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and also the addition salts thereof with an acid or with a base.

Among the pyrimidine derivatives that can be used, non-limiting mention may be made of the compounds described, for example, in German Patent No. DE 2 359 399; Japanese Patent Nos. JP 88-169 571 and JP 05-63124; European Patent No. EP 0 770 375 or Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine; and pyrazolopyrimidine derivatives such as those mentioned in French Patent Application No. FR-A-2,750,048 and among which non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, and the addition salts thereof with an acid and the tautomeric forms thereof, when a tautomeric equilibrium exists.

Among the pyrazole derivatives that may be used, non-limiting mention may be made of the compounds described in German Patent Nos. DE 3,843,892 and DE 4,133,957 and Patent Application Nos. WO 94/08969, WO 94/08970, FR-A-2,733,749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methyl pyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the acid addition salts thereof.

When present in the dye compositions of the present disclosure, the at least one additional oxidation base can be present, for example, in an individual amount ranging from 0.001% to 10% by weight, relative to the weight of the dye composition, such as ranging from 0.005% to 6% by weight, relative to the weight of the dye composition.

As disclosed above, the dye composition of the present disclosure optionally comprises at least one coupler.

Among the couplers that may be used, non-limiting mention may be made of, for example, meta-phenylenediamines, meta-aminophenols, meta-diphenols, naphthalene-based couplers, heterocyclic couplers, for instance indole derivatives, indoline derivatives, sesamol and its derivatives, pyridine derivatives, pyrazolotriazole derivatives, pyrazolones, and the addition salts thereof.

Non-limiting examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene and the acid addition salts thereof.

In the dye composition as disclosed herein, the at least one coupler can be present in an individual amount ranging from 0.001% to 10% by weight, relative to the weight of the dye composition, such as ranging from 0.005% to 6% by weight, relative to the total weight of the dye composition.

As stated previously, the addition salts of the additional oxidation bases and of the couplers may be chosen for example, from the addition salts with an acid, such as the hydrochlorides, hydrobromides, sulfates, citrates, succinates, tartrates, lactates, tosylates, benzenesulfonates, phosphates and acetates.

The dye composition according to the present disclosure may further optionally comprise at least one direct dye, for example, chosen from anionic, cationic and nonionic species.

Non-limiting examples of direct dyes that may be mentioned include nitrobenzene dyes, azo dyes, azomethine dyes, azine dyes, methine dyes, tetraazapentamethine dyes, quinone dyes, anthraquinone dyes, naphthoquinone dyes, benzoquinone dyes, phenothiazine dyes, indigoid dyes, indoamine dyes, xanthene dyes, phenanthridine dyes, phthalocyanin dyes, triarylmethane-based dyes and natural dyes, alone or as mixtures.

Among the nitro chromophores that may be used according to the present disclosure, mention may be made in a non-limiting manner of the radicals derived from the following compounds:
1,4-diamino-2-nitrobenzene,
1-amino-2-nitro-4-β-hydroxyethylaminobenzene,
1-amino-2-nitro-4-bis(β-hydroxyethyl)aminobenzene,
1,4-bis(β-hydroxyethylamino)-2-nitrobenzene,
1-β-hydroxyethylamino-2-nitro-4-bis(β-hydroxyethylamino)benzene,
1-β-hydroxyethylamino-2-nitro-4-aminobenzene,
1-β-hydroxyethylamino-2-nitro-4-(ethyl)(β-hydroxyethyl)aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-[tris(hydroxymethyl)methylamino]-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-[bis(β-hydroxyethyl)amino]-3-nitrobenzene,
1-β-hydroxyethylamino-2-nitrobenzene, and
1-hydroxy-4-β-hydroxyethylamino-3-nitrobenzene.

Among the azo direct dyes, non-limiting mention may be made of those described in Patent Application Nos. WO 95/15144, WO 95/01772 and EP 714 954. Among the azo dyes that may also be used, further non-limiting mention may be made of the following dyes described in the Color Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9. Non-limiting mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Among the quinone dyes that may be used, non-limiting mention may be made of the radicals derived from the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone.

Among the azine direct dyes that may be used, non-limiting mention may be made of the following compounds: Basic Blue 17, and Basic Red 2.

Among the indoamine direct dyes that may be used as disclosed herein, non-limiting mention may be made of the following compounds: 2-β-hydroxyethylamino-5-[bis(β4'-hydroxyethyl)amino]anilino-1,4-benzoquinone; 2-β-hydroxyethylamino-5-(2'-methoxy-4'-amino)anilino-1,4-benzoquinone; 3-N-(2'-chloro-4'-hydroxy)phenylacetylamino-6-methoxy-1,4-benzoquinoneimine; 3-N-(3'-chloro-4'-methylamino)phenylureido-6-methyl-1,4-benzoquinoneimine; 3-[4'-N-(ethylcarbamylmethyl)amino]phenylureido-6-methyl-1,4-benzoquinoneimine.

Further non-limiting mention may also be made of the dyes described in U.S. Pat. No. 5,888,252, European Patent Nos. EP 1,133,975, EP 860 636, and EP 714 954, and International Application Nos. WO 03/029359, WO 95/01772, and WO 95/15144. Non-limiting mention may also be made of those mentioned in the encyclopaedia *The Chemistry of Synthetic Dye* by K. Venkataraman, 1952, Academic Press, vol. 1 to 7, in encyclopaedia "Kirk-Othmer" "Chemical Technology," in the chapter "Dyes and Dye Intermediate," 1993, Wiley & Sons, and in various chapters of the encyclopaedia *Ullmann's Encyclopaedia of Industrial Chemistry,* 7th edition, Wiley & Sons.

When they are present in the dye composition as disclosed herein, the at least one direct dye may be present in an amount ranging from 0.001% to 20% by weight, relative to the total weight of the dye composition, such as from 0.01% to 10% by weight, relative to the total weight of the dye composition.

The medium that is suitable for dyeing, also known as the dye support, is a cosmetic medium that generally comprises of water or comprises a mixture of water and at least one organic solvent to dissolve the compounds that would not be sufficiently soluble in water. Among the organic solvents that may be used, non-limiting mention may be made, for example, of $C_1$-$C_4$ alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

The at least one solvent, if present, can be present in an amount ranging from 1% to 40% by weight, relative to the total weight of the dye composition, such as ranging from 5% to 30% by weight.

The dye composition of the present disclosure may also comprise at least one oxidizing agent.

The oxidizing agents conventionally used for the oxidation dyeing of keratin fibers include, for example, hydrogen peroxide, urea peroxide, alkali metal bromates, persalts such as perborates and persulfates, peracids and oxidase enzymes, among which non-limiting mention may be made of peroxidases, 2-electron oxidoreductases such as uricases, and 4-electron oxygenases, for instance laccases. In one embodiment of the present disclosure, hydrogen peroxide is used.

The dye composition in accordance with the present disclosure can also comprise at least one adjuvant conventionally used in compositions for dyeing the hair, such as anionic, cationic, nonionic, amphoteric or zwitterionic surfactants or mixtures thereof; anionic, cationic, nonionic, amphoteric or zwitterionic polymers or mixtures thereof; inorganic or organic thickeners, such as anionic, cationic, nonionic and amphoteric associative polymeric thickeners; antioxidants; penetration agents; sequestering agents; fragrances; buffers; dispersing agents; packaging agents such as, for example, silicones, which may or may not be volatile or modified; film-forming agents; ceramides; preserving agents; and opacifiers.

When present in the dye composition, the at least one adjuvant can be present in an individual amount ranging from 0.01% to 20% by weight, relative to the weight of the composition.

A person skilled in the art will take care to select any additional compounds such that the beneficial properties associated with the dye composition in accordance with the present disclosure are not, or are not substantially, adversely affected by the addition(s) envisaged.

The pH of the dye composition in accordance with the present disclosure can range from 3 to 12, for instance, from 5 to 11. It may be adjusted to the desired value using acidifying or basifying agents usually used in the dyeing of keratin fibers, or alternatively using standard buffer systems.

Among the acidifying agents that may be used, non-limiting mention may be made, for example, of inorganic or organic acids such as hydrochloric acid, orthophosphoric acid, sulfuric acid, carboxylic acids such as acetic acid, tartaric acid, citric acid and lactic acid, and sulfonic acids.

Among the basifying agents that may be used, non-limiting mention may be made, for example, of aqueous ammonia, alkaline carbonates, alkanolamines such as mono-, di- and triethanolamine and derivatives thereof, sodium hydroxide, potassium hydroxide and the compounds of formula (II):

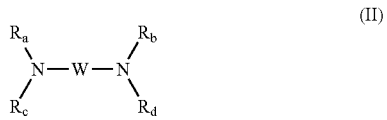

(II)

wherein W is a propylene residue that is unsubstituted or substituted with a hydroxyl group or a $C_1$-$C_4$ alkyl radical; $R_a$, $R_b$, $R_c$ and $R_d$, which may be identical or different, are chosen from hydrogen atoms, $C_1$-$C_4$ alkyl radicals and $C_1$-$C_4$ hydroxyalkyl radicals.

The dye composition according to the present disclosure may be in various forms, such as in the form of liquids, creams or gels, or in any other form that is suitable for dyeing keratin fibers, such as human hair.

The process according to the present disclosure comprises applying a composition as disclosed herein to wet or dry keratin fibers.

It should be noted that when using an oxidizing agent, it may be added to the dye composition at the time of use, or it may be implemented using an oxidizing composition comprising it, applied simultaneously or sequentially to the dye composition as disclosed herein. In the latter case, the at least one oxidizing agent is comprised in a composition other than the dye composition as disclosed herein.

According to one embodiment of the process according to the present disclosure, the dye composition is mixed, for example at the time of use, with a composition comprising, in a medium that is suitable for dyeing, at least one oxidizing agent, this oxidizing agent being present in an amount that is sufficient to obtain the desired coloration. The mixture obtained is then applied to the keratin fibers. After an action time ranging from 3 to 50 minutes, such as from 5 to 30 minutes, the keratin fibers are rinsed, optionally washed, for example, with shampoo, rinsed again and then dried or allowed to dry.

The oxidizing composition may also comprise at least one adjuvant conventionally used in compositions for dyeing the hair and as defined above.

The pH of the oxidizing composition comprising the at least one oxidizing agent is such that, after mixing with the dye composition, the pH of the resulting composition applied to the keratin fibers ranges for example, from 3 to 12, such as from 5 to 11. It may be adjusted to the desired value by means of acidifying or basifying agents usually used in the dyeing of keratin fibers and as defined above.

The ready-to-use composition that is finally applied to the keratin fibers, and which corresponds to the dye composition mixed with the composition comprising the at least one oxidizing agent, may be in various forms, such as in the form of liquids, creams or gels or any other form that is suitable for dyeing keratin fibers, for instance human hair.

Another aspect of the present disclosure is a multi-compartment dyeing device or "kit," in which a first compartment comprises a dye composition comprising at least one compound of formula (I') as defined above and a second compartment comprises at least one oxidizing agent.

This kit may be equipped with an applicator for applying the desired mixture to the hair, such as the devices described in French Patent No. FR-2,586,913.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific example are reported as precisely as possible. Any numerical value, however, inherently contain certain errors necessarily resulting from the standard deviation found in their respective testing measurements.

The following examples are intended to illustrate the invention in a non-limiting manner.

EXAMPLES

Example 1

Synthesis of 1,3-bis(4-aminophenylamino)propane tetrahydrochloride (2)

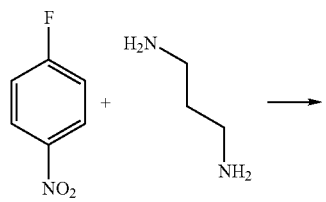

Step 1: Synthesis of N,N'-bis(4-nitrophenyl)-1,3-propanediamine (1)

5 g of 4-fluoronitrobenzene (35 mmol) were dissolved in 5 ml of DMSO. 1 equivalent of 1,3-diaminopropane and 2.2 equivalents of triethylamine were added to the solution. The reaction medium was maintained at 60° C. for 20 hours. The mixture was then poured onto crushed ice, and a precipitate formed. This precipitate was filtered off, washed with water and then dried.

Step 2: Synthesis of 1,3-bis(4-aminophenylamino)propane tetrahydrochloride (2)

In a 1 liter hydrogenator, the nitro compound (1) was dissolved in 500 ml of ethanol. 10% palladium on charcoal (50% water) was added and the hydrogenator was charged with hydrogen. After reaction for 1 hour 30 minutes, the palladium was filtered off and 20 ml of 3M hydrochloric ethanol and then 300 ml of isopropyl ether were added to the filtrate. The precipitate obtained was filtered off and recrystallized from hydrochloric ethanol.

The proton NMR and mass spectra were in accordance with the expected product.

Example 2

Synthesis of 1,3-bis(4-aminophenylamino)pentane tetrahydrochloride (4)

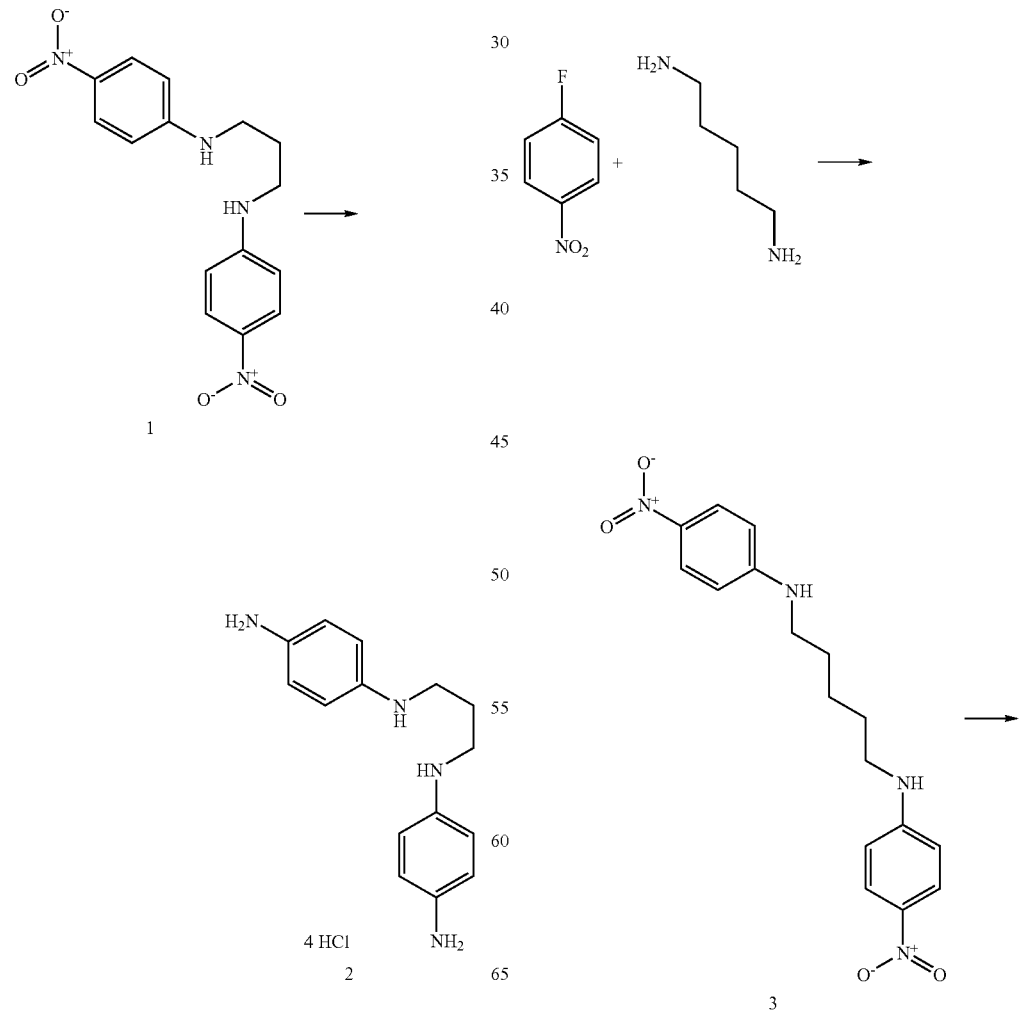

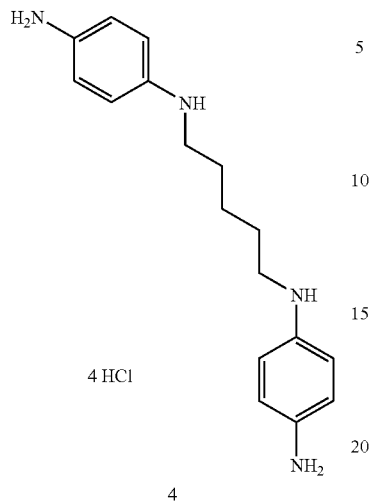

4

Step 1: Synthesis of N,N'-bis(4-nitrophenyl-1,3-pentanediamine (3)

1.15 g of 4-fluoronitrobenzene (8.15 mmol) were dissolved in 5 ml of DMSO. 1 equivalent of 1,5-diaminopentane and 4 equivalents of triethylamine were added to the solution. The reaction medium was maintained at 60° C. for 20 hours. The mixture was then poured onto crushed ice, and a precipitate formed. This precipitate was filtered off, washed with water and then dried.

Step 2: Synthesis of 1,3-bis(4-aminophenylamino)pentane tetrahydrochloride (4)

In a 1 liter hydrogenator, the nitro compound (3) was dissolved in 500 ml of ethanol. 10% palladium on charcoal (50% water) was added and the hydrogenator was charged with hydrogen. After reaction for 1 hour 30 minutes, the palladium was filtered off and 20 ml of 3M hydrochloric ethanol and then 300 ml of isopropyl ether were added to the filtrate. The precipitate obtained was filtered off and recrystallized from hydrochloric ethanol.

The proton NMR and mass spectra were in accordance with the expected structure of the product.

Example 3

Synthesis of N4-{3-[(4-amino-3-methylphenyl)amino]propyl}-2-methylbenzene-1,4-diamine tetrahydrochloride (6)

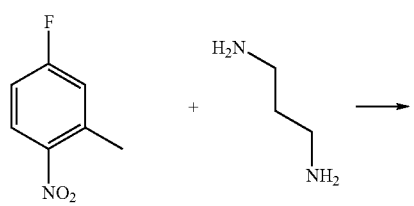

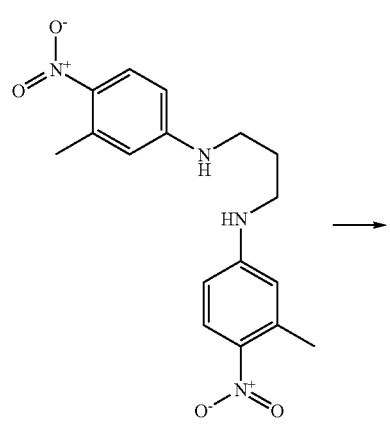

5

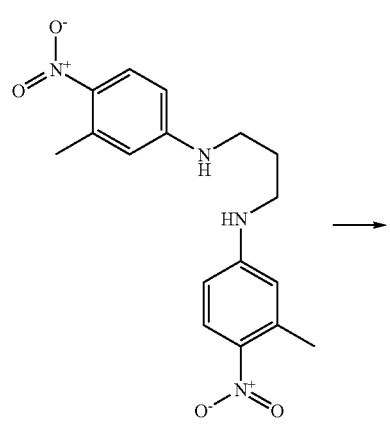

6

Step 1: Synthesis of N,N'-bis(3-methyl-4-nitrophenyl)-1,3-propanediamine (5)

1.5 g of 5-fluoro-2-nitrotoluene (9.67 mmol) were dissolved in 10 ml of DMSO. 1.2 equivalents of 1,3-diaminopropane and 1.2 equivalents of triethylamine were added to the solution. The reaction medium was maintained at 80° C. for 24 hours. The mixture was then poured onto crushed ice, and a precipitate formed. This precipitate was filtered off, washed with water and then dried.

Step 2: Synthesis of N4-{3-[(4-amino-3-methylphenyl)amino]propyl}-2-methylbenzene-1,4-diamine tetrahydrochloride (6)

The product obtained during the preceding step, compound (5), was reduced with a boiling zinc/ammonium chloride/water/ethanol mixture. The corresponding amine was isolated in tetrahydrochloride form.

The proton NMR and mass spectra were in accordance with the expected structure of the product.

Example 4

Synthesis of N1-{3-[(4-amino-2-methylphenyl)amino]propyl}-2-methylbenzene-1,4-diamine tetrahydrochloride (8)

Example 5

Synthesis of N4-{5-[(4-amino-3-methylphenyl)amino]pentyl}-2-methylbenzene-1,4-diamine tetrahydrochloride (10)

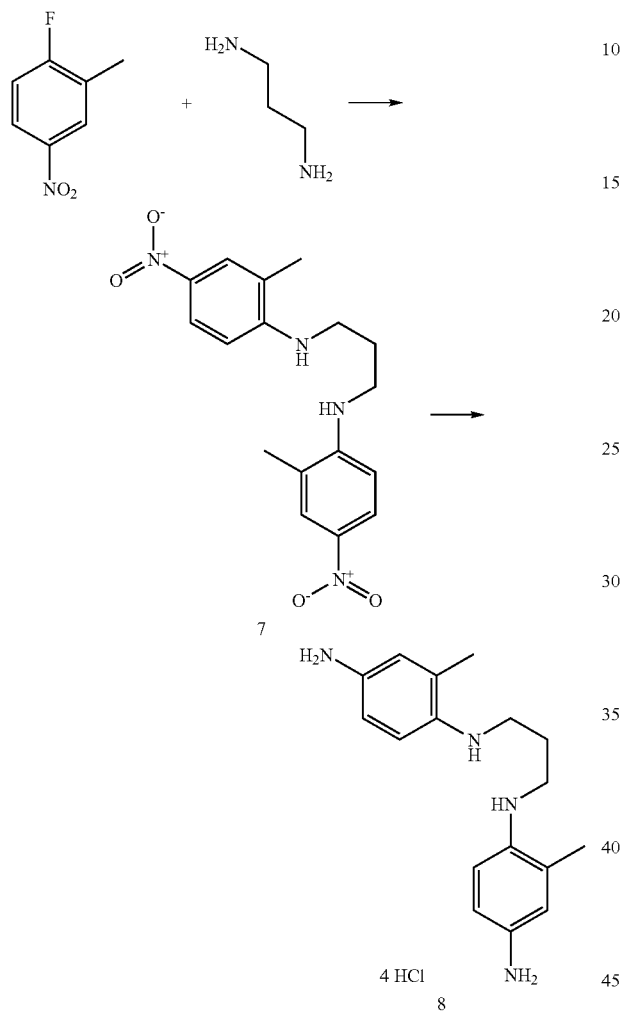

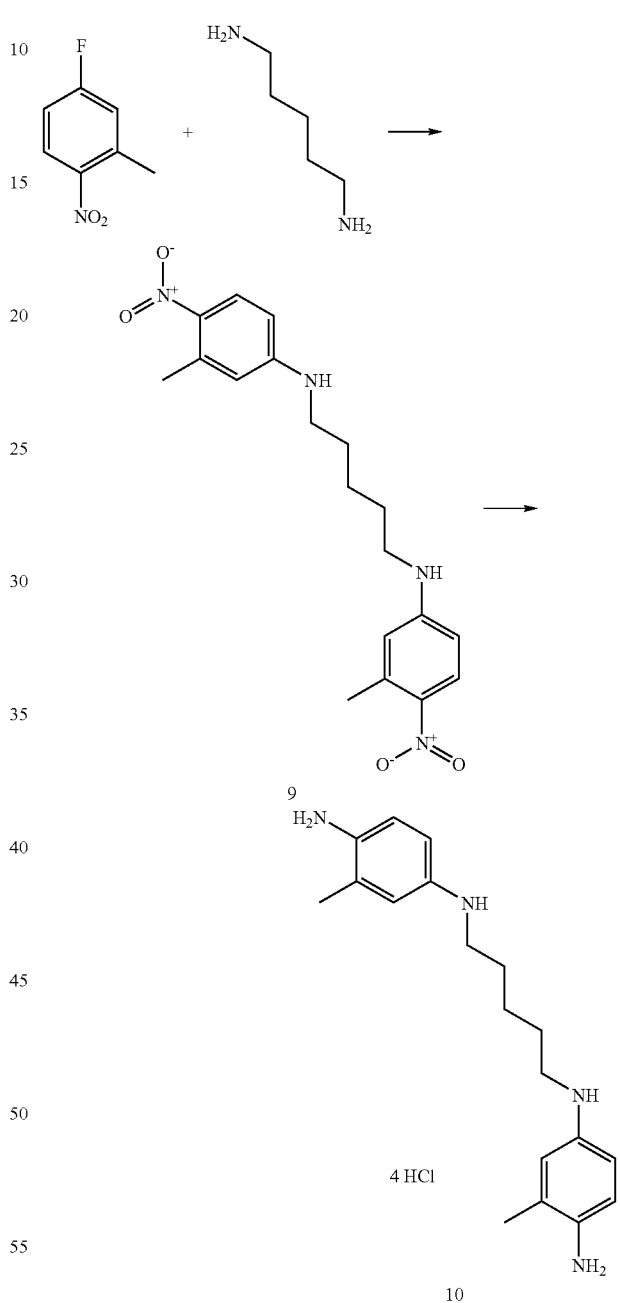

Step 1: Synthesis of N,N'-bis(2-methyl-4-nitrophenyl)-1,3-propanediamine (7)

1.5 g of 2-fluoro-5-nitrotoluene (9.67 mmol) were dissolved in 10 ml of DMSO. 1 equivalent of 1,3-diaminopropane and 1.2 equivalents of triethylamine were added to the solution. The reaction medium was maintained at 80° C. for 24 hours. The mixture was then poured onto crushed ice, and a precipitate formed. This precipitate was filtered off, washed with water and then dried.

Step 2: Synthesis of N1-{3-[(4-amino-2-methylphenyl)amino]propyl}-2-methylbenzene-1,4-diamine tetrahydrochloride (8)

The product obtained during the preceding step, compound (7), was reduced with a boiling zinc/ammonium chloride/water/ethanol mixture. The corresponding amine was isolated in tetrahydrochloride form.

The proton NMR and mass spectra were in accordance with the expected structure of the product.

Step 1: Synthesis of N,N'-bis(3-methyl-4-nitrophenyl)-1,5-pentanediamine (9)

1.5 g of 5-fluoro-2-nitrotoluene (9.67 mmol) were dissolved in 10 ml of DMSO. 1.2 equivalents of 1,5-diaminopentane and 1.2 equivalents of triethylamine were added to the solution. The reaction medium was maintained at 80° C. for 24 hours. The mixture was then poured onto crushed ice, and a precipitate formed. This precipitate was filtered off, washed with water and then dried.

Step 2: Synthesis of N4-{5-[(4-amino-3-methylphenyl)amino]pentyl}-2-methylbenzene-1,4-diamine tetrahydrochloride (10)

The product obtained during the preceding step, compound (9), was reduced with a boiling zinc/ammonium chloride/water/ethanol mixture. The corresponding amine was isolated in tetrahydrochloride form.

The proton NMR and mass spectra were in accordance with the expected structure of the product.

Example 6

Synthesis of N1-{5-[(4-amino-2-methylphenyl)amino]pentyl}-2-methylbenzene-1,4-diamine tetrahydrochloride (12)

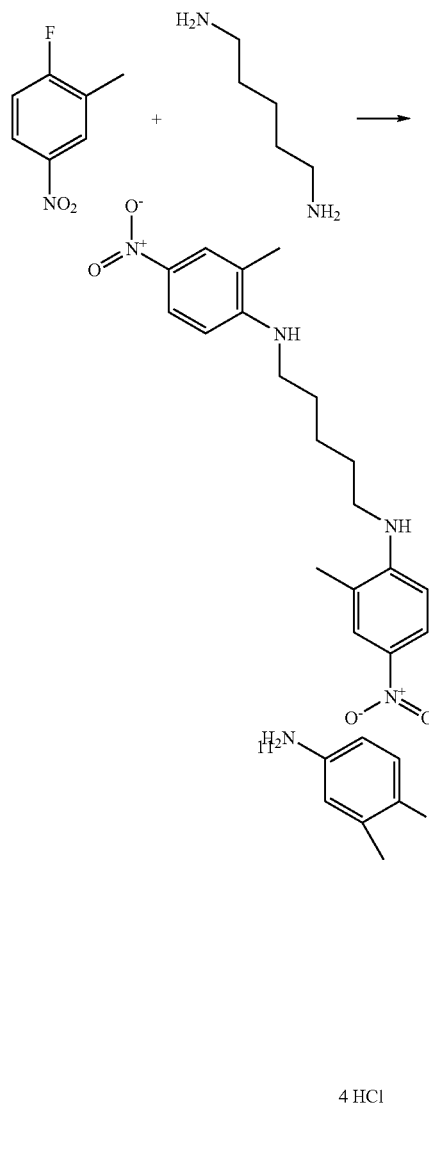

Step 1: Synthesis of N,N'-bis(2-methyl-4-nitrophenyl)-1,5-pentanediamine (11)

1.5 g of 2-fluoro-5-nitrotoluene (9.67 mmol) were dissolved in 10 ml of DMSO. 1.2 equivalents of 1,5-diaminopentane and 1.2 equivalents of triethylamine were added to the solution. The reaction medium was maintained at 80° C. for 24 hours. The mixture was then poured onto crushed ice, and a precipitate formed. This precipitate was filtered off, washed with water and then dried.

Step 2: Synthesis of N1-{5-[(4-amino-2-methylphenyl)amino]pentyl}-2-methylbenzene-1,4-diamine tetrahydrochloride (12)

The product obtained during the preceding step, compound (11), was reduced with a boiling zinc/ammonium chloride/water/ethanol mixture. The corresponding amine was isolated in tetrahydrochloride form.

The proton NMR and mass spectra were in accordance with the expected structure of the product.

Example 7

Synthesis of N4-{7-[(4-amino-3-methylphenyl)amino]heptyl}-2-methylbenzene-1,4-diamine tetrahydrochloride (14)

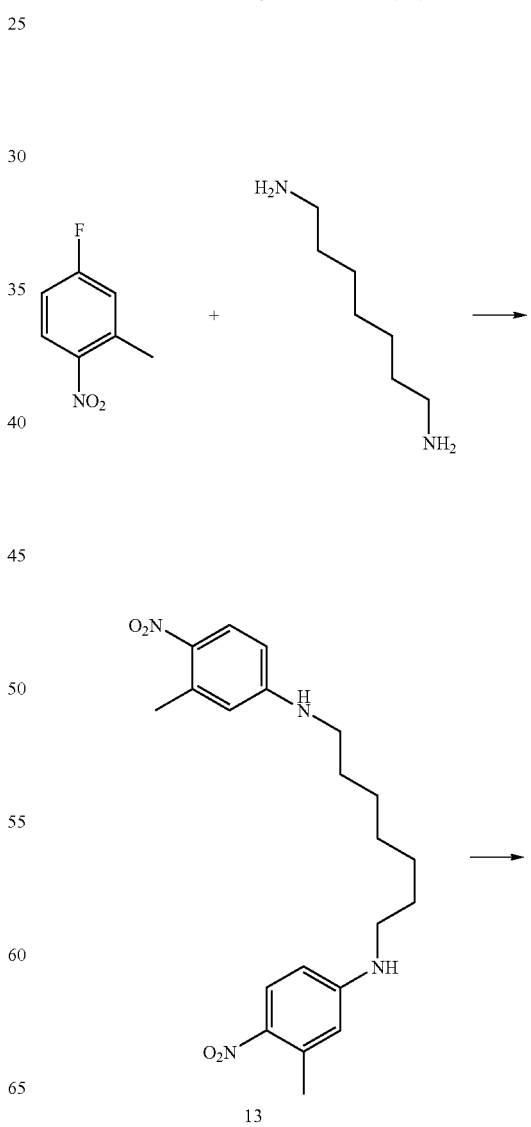

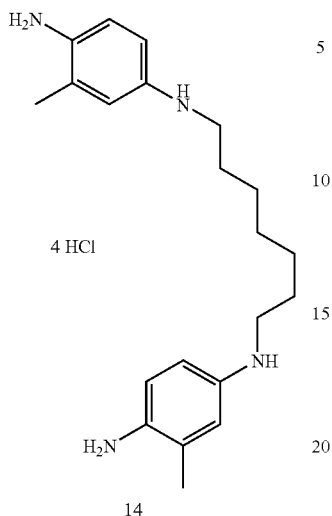

14

Step 1: Synthesis of N,N'-bis(3-methyl-4-nitrophenyl)-1,7-heptanediamine (13)

1.5 g of 5-fluoro-2-nitrotoluene (9.67 mmol) were dissolved in 10 ml of DMSO. 1.2 equivalents of 1,7-diaminoheptane and 1.2 equivalents of triethylamine were added to the solution. The reaction medium was maintained at 80° C. for 24 hours. The mixture was then poured onto crushed ice, and a precipitate formed. This precipitate was filtered off, washed with water and then dried.

Step 2: Synthesis of N4-{7-[(4-amino-3-methylphenyl)amino]heptyl}-2-methylbenzene-1,4-diamine tetrahydrochloride (14)

The product obtained during the preceding step, compound (13), was reduced with a boiling zinc/ammonium chloride/water/ethanol mixture. The corresponding amine was isolated in tetrahydrochloride form.

The proton NMR and mass spectra were in accordance with the expected structure of the product.

Example 8

Synthesis of N1-{7-[(4-amino-2-methylphenyl)amino]heptyl}-2-methylbenzene-1,4-diamine tetrahydrochloride (16)

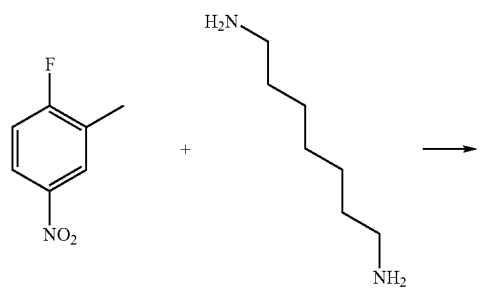

Step 1: Synthesis of N,N'-bis(2-methyl-4-nitrophenyl)-1,7-heptanediamine (15)

1.5 g of 2-fluoro-5-nitrotoluene (9.67 mmol) were dissolved in 10 ml of DMSO. 1.2 equivalents of 1,7-diaminoheptane and 1.2 equivalents of triethylamine were added to the solution. The reaction medium was maintained at 80° C. for 24 hours. The mixture was then poured onto crushed ice, and a precipitate formed. This precipitate was filtered off, washed with water and then dried.

Step 2: Synthesis of N1-{7-[(4-amino-2-methylphenyl)amino]heptyl}-2-methylbenzene-1,4-diamine tetrahydrochloride (16)

The product obtained during the preceding step, compound (15), was reduced with a boiling zinc/ammonium chloride/water/ethanol mixture. The corresponding amine was isolated in tetrahydrochloride form.

The proton NMR and mass spectra were in accordance with the expected structure of the product.

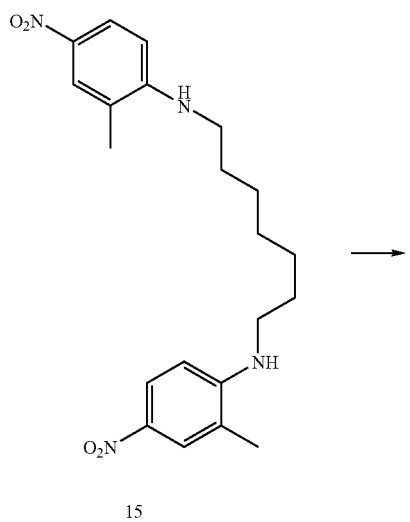

16

Examples of Dyeing

The following compositions were prepared:

| Constituent | Amount |
| --- | --- |
| Double para-phenylenediamine (*) | $3 \times 10^{-3}$ mol % |
| 2,4-Diaminophenoxyethanol dihydrochloride (Coupler ($6 \times 10^{-3}$ mol)) | 1.45 g % |
| Oleyl alcohol polyglycerolated with 2 mol of glycerol | 4 g % |
| Oleyl alcohol polyglycerolated with 4 mol of glycerol | 5.69 g % AM |
| Oleic acid | 3 g % |
| Oleylamine containing 2 mol of ethylene oxide, sold under the trade name Ethomeen 012 by the company Akzo | 7 g % |
| Diethylaminopropyl laurylaminosuccinamate, sodium salt, containing 55% AM | 3.0 g % AM |
| Oleyl alcohol | 5 g % |
| Oleic acid diethanolamide | 12 g % |
| Ethyl alcohol | 7 g % |
| Propylene glycol | 3.5 g % |
| Dipropylene glycol | 0.5 g % |
| Propylene glycol monomethyl ether | 9 g % |
| Antioxidant/sequestering agent | qs |
| Ammonium acetate | 0.8 g % |
| Sodium metabisulfite as an aqueous 35% solution | 0.45 g % |
| 20% aqueous ammonia | 10 g % |
| Demineralized water      qs | 100 g % |

(*) First Series of Tests:

Compositions comprising the following compounds were compared:
- the compound obtained in Example 1: 1,3-bis(4-aminophenylamino)propane. tetrahydrochloride (2) (hereinafter "invention compound C3" or "C3") was first compared with a comparative compound C2: 1,2-bis(4-aminophenylamino)ethane tetrahydrochloride, and
- was second compared with a comparative compound C4: 1,4-bis(4-aminophenylamino)butane tetrahydrochloride.

(*) Second Series of Tests:

Compositions comprising the following compounds were compared:
- the compound obtained in Example 2: 1,5-bis(4-aminophenylamino)pentane tetrahydrochloride (hereinafter "invention compound C5" or "C5") was first compared with the a comparative compound C4, and
- was second compared with a comparative compound C6: 1,6-bis(4-aminophenylamino)hexane tetrahydrochloride.

The comparative compounds were obtained in a manner similar to that detailed in Examples 1 and 2.

Each composition was then mixed with 20-volumes aqueous hydrogen peroxide cream (at equal weight) and then applied to locks of natural (NG) and permanent-waved (PWG) hair containing 90% grey hairs.

The leave-in time was 30 minutes and the "formula/locks" bath ratio was 10.

The locks of hair were subsequently washed with a shampoo and then dried.

Results Obtained:

After drying, the increase in color was evaluated visually, noting that a blue color was obtained for each composition.

It was similarly evaluated by measuring the L*a*b* (CM 2002 colorimeter, illuminant D65-10° CSI).

The value of L*, which ranges from 0 (dark) to 100 (light), was measured. The more colored the hair, the smaller the value of L*.

The selectivity was calculated according to the following formula:

$$\text{selectivity} = \sqrt{(L^*_{NG} - L^*_{PWG})^2 + (a^*_{NG} - a^*_{PWG})^2 + (b^*_{NG} - b^*_{PWG})^2}$$

iwherein $L^*_{NG}$, $a^*_{NG}$ and $b^*_{NG}$ represent the colorimetric values on natural hair containing 90% grey hairs, and $L^*_{PWG}$, $a^*_{PWG}$ and $b^*_{PWG}$ represent the calorimetric values on permanent-waved hair containing 90% grey hairs.

The tables below summarize the results obtained:

| First series of tests | | | | |
| --- | --- | --- | --- | --- |
| | L* | a* | b* | Selectivity |
| Undyed hair | 55.34 | 0.62 | 11.60 | |
| C3 invention | 26.17 | −0.13 | −10.59 | 6.70 |
| C2 comparative | 40.34 | −0.47 | −3.23 | 9.27 |
| C4 comparative | 29.05 | −0.29 | −13.50 | 9.92 |

| Second series of tests | | | | |
| --- | --- | --- | --- | --- |
| | L* | a* | b* | Selectivity |
| Undyed hair | 55.34 | 0.62 | 11.60 | |
| C5 invention | 21.57 | 2.37 | −9.97 | 6.05 |
| C4 comparative | 29.05 | −0.29 | −13.50 | 9.92 |
| C6 comparative | 36.99 | −2.79 | −4.56 | 8.81 |

These results show that the compositions according to the present disclosure lead to a better uptake in dye, due to the lower value of L* in the case of the compositions according to the present disclosure.

Furthermore, the compositions according to the present disclosure lead to better uniformity of the color, since the selectivity values are lower than those obtained with the compositions comprising the comparative compounds.

Dyeing Examples 1.1 to 1.9

| | Examples | | | | | | | | |
| --- | --- | --- | --- | --- | --- | --- | --- | --- | --- |
| | 1.1 | 1.2 | 1.3 | 1.4 | 1.5 | 1.6 | 1.7 | 1.8 | 1.9 |
| N4-{3-[(4-Amino-3-methyl-phenyl)amino]-propyl}-2-methyl-benzene-1,4-diamine tetrahydrochloride 6 | $10^{-3}$ mol | $10^{-3}$ mol | | | | | | | |

-continued

| | Examples | | | | | | | | |
|---|---|---|---|---|---|---|---|---|---|
| | 1.1 | 1.2 | 1.3 | 1.4 | 1.5 | 1.6 | 1.7 | 1.8 | 1.9 |
| N4-{5-[(4-Amino-3-methylphenyl)-amino]pentyl}-2-methylbenzene-1,4-diamine tetrahydrochloride 10 | | | $10^{-3}$ mol | $10^{-3}$ mol | | | | | |
| N1-{5-[(4-Amino-2-methylphenyl)-amino]pentyl}-2-methylbenzene-1,4-diamine tetrahydrochloride 12 | | | | | $10^{-3}$ mol | | | | |
| N4-{7-[(4-Amino-3-methylphenyl)-amino]heptyl}-2-methylbenzene-1,4-diamine tetrahydrochloride 14 | | | | | | $10^{-3}$ mol | $10^{-3}$ mol | | |
| N1-{7-[(4-Amino-2-methylphenyl)-amino]heptyl}-2-methylbenzene-1,4-diamine tetrahydrochloride 16 | | | | | | | | $10^{-3}$ mol | $10^{-3}$ mol |
| 2-(2,4-Diaminophenoxy)-ethanol dihydrochloride | $10^{-3}$ mol | $10^{-3}$ mol | $10^{-3}$ mol | $10^{-3}$ mol | $10^{-3}$ mol | $10^{-3}$ mol | $10^{-3}$ mol | $10^{-3}$ mol | $10^{-3}$ mol |
| Dye support* | (1) | (2) | (1) | (2) | (1) | (1) | (2) | (1) | (2) |
| Demineralized water qs | 100 g | 100 g | 100 g | 100 g | 100 g | 100 g | 100 g | 100 g | 100 g |
| Shade obtained | Strong blue-green grey | Blue-green | Strong blue-grey | Strong blue | Grey | Strong blue-green grey | Strong blue | Grey | Blue-green grey |

| (*): dye support (1) pH 7 | |
|---|---|
| 96° ethyl alcohol | 20.8 g |
| Sodium metabisulfite as an aqueous 35% solution | 0.23 g AM |
| Pentasodium salt of diethylenetriaminepentaacetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

| (*): dye support (2) pH 9.5 | |
|---|---|
| 96° ethyl alcohol | 20.8 g |
| Sodium metabisulfite as an aqueous 35% solution | 0.23 g AM |
| Pentasodium salt of diethylenetriaminepentaacetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% of grey hairs. After a leave-in time of 30 minutes, the locks were rinsed, washed with a standard shampoo, rinsed again and then dried.

The shades obtained are given in the above table.

What is claimed is:

1. A dye composition comprising, in a medium that is suitable for dyeing keratin fibers, at least one compound chosen from those of formula (I') and the addition salts thereof:

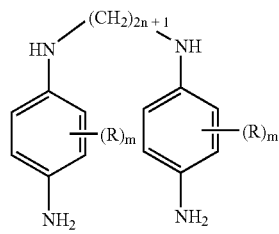

wherein:
R, which may be identical or different, is chosen from $C_1$-$C_2$ alkyl radicals; and $C_1$-$C_2$ alkoxy radicals;
m, which may be identical or different, is an integer ranging from 0 to 4;
n is an integer ranging from 1 to 3.

2. The dye composition according to claim 1, wherein the keratin fibers are human keratin fibers.

3. The dye composition according to claim 1, wherein when n is equal to 1, m does not equal 0.

4. The dye composition according to claim 1, wherein m is equal to 0 or 1.

5. The dye composition according to claim 4, wherein m is equal to 0.

6. The dye composition according to claim 1, where n is equal to 2.

7. The dye composition according to claim 1, where the at least one compound of formula (I') is present in an amount ranging from 0.001% to 10% by weight, relative to the total weight of the dye composition.

8. The dye composition according to claim 7, where the at least one compound of formula (I') is present in an amount ranging from 0.005% to 6% by weight, relative to the weight of the dye composition.

9. The dye composition according to claim 1, further comprising at least one additional oxidation base other than the at least one compound of formula (I'), optionally combined with at least one coupler.

10. The dye composition according to claim 9, where the at least one additional oxidation base is chosen from para-phenylenediamines, bis(phenyl)alkylenediamines other than the compound of formula (I'), para-aminophenols, ortho-aminophenols, heterocyclic bases, and the addition salts thereof.

11. The dye composition according to claim 9, where the at least one additional oxidation base is present in an individual amount ranging from 0.001% to 10% by weight, relative to the total weight of the dye composition.

12. The dye composition according to claim 9, where the at least one coupler is chosen from meta-phenylenediamines, meta-aminophenols, meta-diphenols, naphthalene-based couplers, heterocyclic couplers, and the addition salts thereof.

13. The dye composition according to claim 12, where the at least one coupler is present in an individual amount ranging from 0.001% to 10% by weight, relative to the total weight of the dye composition.

14. The dye composition according to claim 1, further comprising at least one direct dye chosen from neutral, anionic and cationic direct dyes.

15. The dye composition according to claim 14, where the at least one direct dye is chosen from nitrobenzene dyes, azo dyes, azomethine dyes, azine dyes, methine dyes, tetraazapentamethine dyes, quinone dyes, anthraquinone dyes, naphthoquinone dyes, benzoquinone dyes, phenothiazine dyes, indigoid dyes, indoamine dyes, xanthene dyes, phenanthridine dyes, phthalocyanin dyes, triarylmethane-based dyes and natural dyes.

16. The dye composition according to claim 14, where the at least one direct dye is present in an amount ranging from 0.001% to 20% by weight, relative to the total weight of the dye composition.

17. The dye composition according to claim 16, where the at least one direct dye is present in an amount ranging from 0.01% to 10% by weight, relative to the weight of the dye composition.

18. The dye composition according to claim 1, further comprising at least one oxidizing agent.

19. The dye composition according to claim 18, where the at least one oxidizing agent is chosen from hydrogen peroxide, urea peroxide, alkali metal bromates, persalts, and enzymes.

20. The dye composition according to claim 18, where the persalts are chosen from perborates and persulfates.

21. The dye composition according to claim 18, where the enzymes are chosen from peroxidases and two- or four-electron oxidoreductases.

22. The dye composition according to claim 18, where the at least one oxidizing agent is hydrogen peroxide.

23. A process for the oxidation dyeing of keratin fibers, comprising
applying to the wet or dry fibers a dye composition, wherein the dye composition comprises, in a medium that is suitable for dyeing keratin fibers, at least one compound chosen from those of formula (I') and the addition salts thereof:

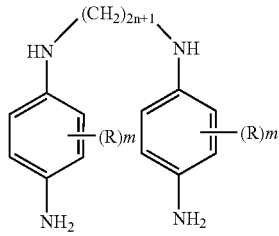

wherein:
R, which may be identical or different, is chosen from $C_1$-$C_2$ alkyl radicals; and $C_1$-$C_2$ alkoxy radicals;
m, which may be identical or different, is an integer ranging from 0 to 4;
n is an integer ranging from 1 to 3; and leaving the composition on the keratin fibers for a time that is sufficient to obtain the desired coloration.

24. The process according to claim 23, where the keratin fibers are human keratin fibers.

25. The process according to claim 23, where the composition, at the time it is applied to the fibers, further comprises at least one oxidizing agent.

26. The process according to claim 25, where the at least one oxidizing agent is in a composition separate from the dye composition prior to the process being performed.

27. A multi-compartment kit for dyeing keratin fibers comprising
a first compartment comprising a dye composition comprising, in a medium that is suitable for dyeing keratin fibers, at least one compound chosen from those of formula (I') and the addition salts thereof:

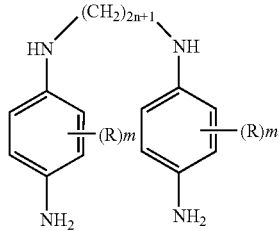

wherein:
R, which may be identical or different, is chosen from $C_1$-$C_2$ alkyl radicals; and $C_1$-$C_2$ alkoxy radicals;
m, which may be identical or different, is an integer ranging from 0 to 4;
n is an integer ranging from 1 to 3; and
a second compartment comprising at least one oxidizing agent.

* * * * *

UNITED STATES PATENT AND TRADEMARK OFFICE
CERTIFICATE OF CORRECTION

PATENT NO. : 7,396,367 B2
APPLICATION NO. : 11/222238
DATED : July 8, 2008
INVENTOR(S) : Radisson et al.

Page 1 of 1

It is certified that error appears in the above-identified patent and that said Letters Patent is hereby corrected as shown below:

Claim 6, col. 24, line 58, "where" should read -- wherein --.
Claim 7, col. 24, line 60, "where" should read -- wherein --.
Claim 8, col. 24, line 64, "where" should read -- wherein --.
Claim 10, col. 25, line 5, "where" should read -- wherein --.
Claim 11, col. 25, line 10, "where" should read -- wherein --.
Claim 12, col. 25, line 14, "where" should read -- wherein --.
Claim 13, col. 25, line 19, "where" should read -- wherein --.
Claim 15, col. 25, line 26, "where" should read -- wherein --.
Claim 16, col. 25, line 34, "where" should read -- wherein --.
Claim 17, col. 25, line 38, "where" should read -- wherein --.
Claim 19, col. 25, line 44, "where" should read -- wherein --.
Claim 20, col. 25, line 48, "where" should read -- wherein --.
Claim 21, col. 25, line 50, "where" should read -- wherein --.
Claim 22, col. 25, line 53, "where" should read -- wherein --.
Claim 24, col. 26, line 24, "where" should read -- wherein --.
Claim 25, col. 26, line 26, "where" should read -- wherein --.
Claim 26, col. 26, line 29, "where" should read -- wherein --.

Signed and Sealed this

Ninth Day of September, 2008

JON W. DUDAS
*Director of the United States Patent and Trademark Office*